United States Patent
Lenz et al.

(10) Patent No.: US 12,226,559 B2
(45) Date of Patent: Feb. 18, 2025

(54) HOLDING MEANS FOR HOLDING AN OXYGENATOR AND A BLOOD PUMP

(71) Applicant: Hemovent GmbH, Aachen (DE)

(72) Inventors: Christof Lenz, Schwarzenbruck (DE); Oliver Marseille, Aachen (DE); Andreas Nobis, Würselen (DE); Stefan Nötzel, Aachen (DE); Thilo Joost, Friedberg (DE); Benedict Hartmann, Düsseldorf (DE); Christof Paul, Münster (DE)

(73) Assignee: Hemovent GmbH, Aachen (DE)

( * ) Notice: Subject to any disclaimer, the term of this patent is extended or adjusted under 35 U.S.C. 154(b) by 1064 days.

(21) Appl. No.: 16/975,356

(22) PCT Filed: Feb. 26, 2019

(86) PCT No.: PCT/EP2019/054732
§ 371 (c)(1),
(2) Date: Aug. 24, 2020

(87) PCT Pub. No.: WO2019/162526
PCT Pub. Date: Aug. 29, 2019

(65) Prior Publication Data
US 2020/0397966 A1    Dec. 24, 2020

(30) Foreign Application Priority Data

Feb. 26, 2018   (DE) .................... 10 2018 001466.6
Jul. 3, 2018    (LU) .................................. 100850

(51) Int. Cl.
*A61M 1/16*    (2006.01)
*A61M 1/36*    (2006.01)

(52) U.S. Cl.
CPC ........ *A61M 1/1698* (2013.01); *A61M 1/1652* (2014.02); *A61M 1/3666* (2013.01); *A61M 2209/082* (2013.01)

(58) Field of Classification Search
CPC .............. A61M 1/1698; A61M 1/1652; A61M 1/3666; A61M 2209/082
See application file for complete search history.

(56) References Cited

U.S. PATENT DOCUMENTS 4,610,656 A    9/1986    Mortensen
5,270,005 A  * 12/1993    Raible .................. A61M 1/267
                                                  604/6.14

(Continued)

FOREIGN PATENT DOCUMENTS

CN      1339975 A      3/2002
CN    101999966 A      4/2011

(Continued)

OTHER PUBLICATIONS

PCT/EP2019/054732 Search Report & Written Opinion dated Aug. 9, 2019.

*Primary Examiner* — Stanton L Krycinski
(74) *Attorney, Agent, or Firm* — Michael J. Brown

(57) ABSTRACT

The invention relates to a holding means for holding an oxygenator and a blood pump. The holding means is characterised by a frame that can be connected with a carrying case housing in a torque-proof way for fitting the oxygenator and the blood pump relative to each other, wherein the frame has a frame section for connection with the oxygenator in a torque-proof way and another frame section for connection with the blood pump in a torque-proof way.

20 Claims, 11 Drawing Sheets

(56) References Cited

U.S. PATENT DOCUMENTS

| | | | |
|---|---|---|---|
| 5,308,320 A * | 5/1994 | Safar | A61M 60/38 604/113 |
| 5,514,335 A * | 5/1996 | Leonard | A61M 60/38 210/321.86 |
| 5,879,316 A | 3/1999 | Safar et al. | |
| 6,306,346 B1 | 10/2001 | Lindsay | |
| 6,387,323 B1 * | 5/2002 | Afzal | A61M 60/232 604/6.14 |
| 6,468,473 B1 * | 10/2002 | Lindsay | A61M 1/3621 604/4.01 |
| 7,022,284 B2 * | 4/2006 | Brian | A61M 1/262 604/6.14 |
| 7,198,751 B2 | 4/2007 | Carpenter et al. | |
| 7,204,958 B2 * | 4/2007 | Olsen | A61M 1/367 604/4.01 |
| 7,476,359 B2 * | 1/2009 | Maianti | A61M 1/1698 604/6.14 |
| 7,846,122 B2 | 12/2010 | Brieske | |
| 8,133,195 B2 * | 3/2012 | Blicke | A61M 60/38 604/6.14 |
| 8,647,291 B2 * | 2/2014 | Ribolzi | A61M 1/3627 604/6.15 |
| 8,795,591 B2 * | 8/2014 | Roller | A61M 1/36 604/6.14 |
| 8,834,399 B2 * | 9/2014 | Muller-Spanka | A61M 1/3627 604/4.01 |
| 8,882,693 B2 * | 11/2014 | Muller-Spanka | A61M 1/1698 604/4.01 |
| 9,011,769 B2 * | 4/2015 | Silvestri | A61M 1/3638 604/6.14 |
| 9,283,311 B2 * | 3/2016 | Takeuchi | A61M 1/1698 |
| 9,408,960 B2 * | 8/2016 | McLevish | A61M 1/1698 |
| 10,293,093 B2 * | 5/2019 | Bonczar | A61M 1/3667 |
| 10,569,002 B2 * | 2/2020 | Bellini | A61M 1/1629 |
| 10,682,446 B2 * | 6/2020 | Askem | F04B 45/047 |
| 10,835,661 B2 * | 11/2020 | Turner | A61M 1/3667 |
| 2004/0219059 A1 * | 11/2004 | Barringer | A61M 1/3627 604/4.01 |
| 2005/0027231 A1 | 2/2005 | Kirchhof | |
| 2009/0099498 A1 * | 4/2009 | Demers | A61M 1/36225 604/4.01 |
| 2013/0226064 A1 * | 8/2013 | Galavotti | A61M 1/3623 604/4.01 |
| 2019/0038825 A1 * | 2/2019 | Muller-Spanka | A61M 1/3612 |
| 2022/0080090 A1 * | 3/2022 | Petralia | A61M 1/3666 |

FOREIGN PATENT DOCUMENTS

| | | |
|---|---|---|
| CN | 206355375 U | 7/2017 |
| CN | 206777568 U | 12/2017 |
| WO | WO-2019162526 A1 | 8/2019 |

* cited by examiner

HOLDING MEANS FOR HOLDING AN OXYGENATOR AND A BLOOD PUMP

CROSS-REFERENCE

This application is a national stage entry of PCT Application No. PCT/EP2019/054732, filed Feb. 26, 2019; which claims priority to German Application No. 10 2018 001 466.6, filed Feb. 26, 2018; and claims priority to Luxembourg Application No. 100850, filed Jul. 3, 2018; which are incorporated herein by reference in their entirety and to which application we claim priority under 35 USC § 120.

BACKGROUND

The invention relates to a holding means for holding an oxygenator and a blood pump. In addition, the invention relates to a carrying case with a holding means. The invention further relates to a heart-lung machine with such a carrying case.

Patients with acute heart failure or acute lung failure can be kept alive through rapid implementation of heart-lung support in order to win time until further treatment can be initiated. For this the patient is connected to an extracorporeal circuit with suitable cannula, which guarantees heart and lung function.

A heart-lung machine consists of a blood pump and an artificial lung. Blood is extracted from the venous vessel network via peripheral or central access with cannula and returned on the venous or arterial side after enrichment with oxygen. Vital organs are supplied with fresh blood in this way, whilst the patient is transported or can be submitted to further treatment.

The blood pump is normally permanently connected with a drive console and drive energy is transmitted from a pump motor to a rotor of the blood pump by a magnetic coupling. Roller pumps are also used, where a pump tube is inserted into the drive console. The artificial lung, also called oxygenator or gas exchanger, is located behind the blood pump in flow direction and is normally permanently fixed on a holder near the blood pump. The oxygenator and the blood pump must be arranged at a specific angle to each other here in order to ensure a problem-free operation of the heart-lung machine. In emergency situations, the oxygenator and the blood pump are transported to the patient and are then aligned with each other on site and a fluid connection of the same is created, which is very time-consuming.

Blood-carrying tubes lead from the patient to and from the drive console. These tubes must be of sufficient length to ensure that the patient can move safely without the tubes becoming kinked or otherwise mechanically stressed. The extraneous surface of the tubes constitutes a load for the blood here, so that the shortest possible tubes are desirable. The long tubes and the plurality of components of the heart-lung machine to be transported can also lead to life-threatening complications in transport situations, as the patient and the above-mentioned components of the heart-lung machine are normally moved separately from each other.

One disadvantage of the known heart-lung machines therefore consists of that unnecessary time elapses in emergency situations before the oxygenator and the blood pump are aligned with each other and the transport of components of the heart-lung machine is complex.

It is therefore the task of the invention to enable faster heart-lung support for a patient with acute lung failure or cardiac arrest and to simplify the transport of the components of the heart-lung machine.

SUMMARY

The task is solved by a holding means of the type mentioned above, which is characterised by a frame that can be connected with a carrying case housing in a torque-proof way for fitting the oxygenator and the blood pump relative to each other, wherein the frame has a frame section for the torque-proof connecting with the oxygenator and another frame section for the torque-proof connecting with the blood pump.

The holding means according to the invention has the advantage that the oxygenator that is not part of the holding means and the blood pump that is not part of the holding means are fixed by the frame, so that a relative movement between the oxygenator and the blood pump is prevented. This offers the advantage that the oxygenator and the blood pump can be fitted to the frame before using it for a patient. An alignment of the oxygenator and the blood pump relative to each other near the patient can thus be omitted, so that the patient can be supported quickly with the lung-heart machine. The oxygenator and the blood pump also no longer need to be transported separately, but can be transported together with the holding means, which simplifies transport. A transport of blood pump and oxygenator directly together with the patient is also possible.

The relative movement between the oxygenator and the blood pump is prevented in that the frame is designed in such a way that the frame section and the other frame section cannot move relative to each other. The frame section and the other frame section can therefore always be connected with each other. This can for example be realised in that the frame section, the other frame section and the rest of the frame are designed as one piece.

In the sense of the invention an oxygenator is understood as a device with which blood is enriched with oxygen and carbon dioxide can be removed from the blood. The lungs can thus be replaced, at least in the short term, by means of the oxygenator.

The connection of the frame section with the oxygenator can be realised through positive locking and/or friction locking. In addition, the connection of the other frame section with the blood pump can be realised through positive locking and/or friction locking. The oxygenator can also be connected with the frame in a positive locking way, in particular through gluing.

With one particular design the holding means can have a handle, which is connected with the frame in a torque-proof way. In particular, the handle and the frame can be designed of a single piece and/or can always be connected with each other. Transport of the oxygenator and the blood pump is simplified further in this way.

The handle can have a guide for guiding a fluid line or several fluid lines. A fluid such as a gas, in particular, oxygen, or a gas mixture, or blood, can flow through the fluid line here. If several fluid lines are provided blood can flow through at least one line and gas, in particular, oxygen or a gas mixture, can flow through another line. The handle can be arranged at one end of the frame. The handle can, in particular, be arranged at the end of the frame that is furthest from the oxygenator and the blood pump.

The guide can be designed in such a way that several fluid lines can be guided, in particular selectively, in the same direction or in different directions. In particular, the fluid lines can be guided in opposing directions by the guide. In addition, the guide can have a cut-out, in which the fluid line can be arranged or in which the fluid lines can be arranged.

The frame can have another guide for guiding the fluid line or several fluid lines. The frame can guide the fluid lines here, through each of which blood flows. The other guide can have another cut-out, in which the fluid line can be arranged, or in which several fluid lines can be arranged.

Providing the guide and/or the other guide can prevent that the fluid line is damaged, or the fluid lines are damaged, in a simple way. The fluid lines can also be fitted in and on the frame with additional disconnectable fittings. The fitting can be positive locking. Belts or clips can, in particular, be used for fitting the fluid lines.

With one particular design, the oxygenator and the blood pump can be arranged by means of the frame section and the other frame section in such a way that the distance between an oxygenator inlet and the handle is shorter than the distance between a blood pump inlet and the handle. The other frame section can, in particular, be positioned in such a way that a flow direction of the blood flowing out of the blood pump faces in the direction of the handle and/or that the blood flows in a direction facing the handle. Blood flowing out of the blood pump thus flows diagonally upwards during the operation of the blood pump and the oxygenator.

A carrying case with a holding means according to the invention is of particular advantage, wherein the holding means is connected with a carrying case housing in a torque-proof way and/or is partly arranged in the carrying case housing. The carrying case housing offers the advantage that the holding means, in particular, the oxygenator and the blood pump, which are connected with the holding means in a torque-proof way, are well protected against chock and/or impact loads. The carrying case housing also acts as a thermal insulator, so that little heat loss occurs. In addition, the carrying case housing acts as an acoustic insulator. A further advantage is that the carrying case can be placed close to the patient and long tubes can thus be avoided. The oxygenator and the blood pump are connected with the frame in a torque-proof way.

With one particular design, the carrying case housing can have a first housing section and/or a second housing section. The first housing section and the second housing section can once again be disconnectably connected with each other in a torque-proof way. The disconnectable connection between the first housing section and the second housing section can be a positive locking and/or a friction locking connection.

The first housing section and/or the second housing section can be made at least partly, in particular completely, from a non-transparent material. The first housing section can comprise at least one foam material here. The second housing section can comprise at least one foam material, in particular, the same foam material as the first housing section. The foam material of the first and/or second housing section can be a hard foam. The foam material has the advantage that the oxygenator and the blood pump are well protected against shock and/or impact loads. The foam material is also a good thermal insulator.

The first housing section can have a first mounting and the second housing section can have a second mounting. The first mounting and the second mounting can form a hollow space, in which part of the frame and/or the oxygenator and/or the blood pump are arranged. Part of the frame and/or the oxygenator and/or the blood pump can, in particular, be at least partly embedded in the first housing section and the second housing section. This prevents in a simple way that the frame and/or the oxygenator and/or the blood pump can move relative to each other and/or to the carrying case housing.

With one particular design, a part of the second mounting receiving the oxygenator can be designed as an opening for the partial release of the oxygenator. In addition, another part of the second mounting receiving the blood pump can be designed as an opening for partly releasing the blood pump. In addition, a further part of the second mounting receiving the frame can be designed as an opening. The openings enable a user to check whether the oxygenator and/or the blood pump work effectively without having to disconnect the second housing section from the first housing section.

In addition, the second housing section can have a recess, which can be designed as an opening. The recess can be formed in such a way that spare parts and/or operating instructions and/or sensors can be arranged in it.

The carrying case can have a closing cover for closing the part of the second mounting and/or the other part of the second mounting and/or the further part of the second mounting and/or the recess. The closing cover can again be disconnectably connected with the second housing section. The closing cover can be arranged on the side of the second housing section facing away from the first housing section.

It is prevented with the closing cover in an easy way that the part of the oxygenator released by the part of the second mounting and/or the part of the blood pump released by the other part of the second mounting and/or the fluid lines running inside the frame are damaged, for example when transporting the carrying case. In addition, the fluid lines can be fluid-connected with the blood pump and/or the oxygenator when the closing cover is removed in a simple way. It is therefore not necessary to separate the two housing sections from each other to connect the fluid lines with the oxygenator and/or the blood pump.

With one particular design, the first housing section and/or the second housing section can have a passage opening, through which the at least one fluid line that is fluid-connected connected with the oxygenator and/or the blood pump leaves the carrying case housing. Alternatively, several fluid lines that are fluid-connected with the oxygenator and/or the blood pump can leave the carrying case through the passage opening. In addition, a part of the frame can extend through the passage opening. The passage opening can be formed by a section of the first mounting and/or a section of the second mounting.

Several, in particular precisely two, fluid lines can be fluid-connected with the patient here. In addition, other fluid lines can be fluid-connected with a gas source, such as for example an oxygen cylinder. Two components are fluid-connected with each other when a gas and/or a fluid can flow from one component into the other component or vice versa. The carrying case, in particular, the oxygenator and/or the blood pump, can be supplied with a gas or a gas mixture, such as for example a mixture of oxygen and air.

The carrying case can have a fluid outlet opening through which a fluid, such as for example, condensate water, can flow out of the first housing section and/or the second housing section. In this way, it can be prevented in a simple way that water collects inside the carrying case.

The carrying case can have a further passage opening, through which at least one branch line extends for supplying blood to an analysis means. Blood branched off upstream or downstream of the oxygenator and to be supplied to the analysis means flows through the branch line. Blood gas analyses can be carried out in the analysis means.

The branch line and/or the fluid lines can be stored in a carrying case housing. The first mounting and the second mounting can, in particular, be designed in such a way that they can receive the branch line and the fluid lines. The branch line and/or the fluid line can be partly pulled out of the carrying case housing to operate the same. The branch line and/or the fluid lines can be connected with at least one retraction element, in particular an elastic element, in the carrying case. The retraction element is designed in such a way that it applies a retraction force to the branch line and/or the fluid line after pulling out the branch line and/or the fluid line, so that the same is pulled back into the carrying case housing after use.

At least one arresting can be present, which can be connected with the fluid line and/or the branch line. The arresting can be arranged at the outer carrying case edge and can ensure that the lines remain in position during use despite the retraction force and can therefore not be pulled into the carrying case. The branch line and/or the fluid lines can be equipped with automatic and removable ventilation valves at one end and can be recloseable. The branch line can be at least 20 cm long.

The carrying case can be ventilated through the passage opening and/or through the further passage opening and/or through the fluid outlet opening, in particular prior to commissioning the carrying case. This can take place automatically when the carrying case is for example placed on a horizontal surface.

The carrying case can have a footprint that is arranged and designed in such a way that the oxygenator inlet is arranged in a vertical direction, in particular, in the direction of gravity, above the blood pump outlet when the carrying case is placed on a positioning surface with its footprint. The positioning surface can be the floor on which the carrying case is placed during use. As a result, the placing of the carrying case on the positioning surface with its footprint can align the holding means in such a way that the oxygenator inlet is arranged above the blood pump outlet.

With one particular design, the blood pump can be driven currentless. This means that the blood pump is not supplied with electric energy. The blood pump can be driven by means of the gas flowing in the fluid line here. As a result, a carrying case that needs to be connected only with a gas source and/or a device for controlling or regulating the gas volume flow supplied to the oxygenator and/or blood pump is realised, so that the oxygenator and the blood pump can be operated.

Alternatively, the use of a blood pump driven by means of electricity is possible. For this at least one electric energy store can be arranged in the carrying case, which supplies the blood pump with electric energy. Alternatively, the blood pump can be electrically connected with an energy source arranged outside of the carrying case by means of electric cables.

The blood pump can be designed as a pulsatile displacement pump or as a rotation pump.

The blood pump and the oxygenator can be fluid-connected with each other. The blood pump can be positioned fluidically upstream of the oxygenator here. The blood extracted from the patient can, in particular, flow through the blood pump and then through the oxygenator here. Blood then flows from the oxygenator back to the patient.

A blood pump inlet can be fluid-connected with a first line of the fluid lines, in particular, directly. Another end of the first line can be fluid-connected with the patient, in particular, directly. The blood pump can be fluid-connected with the oxygenator by means of a second line of the fluid lines. An oxygenator outlet can be fluid-connected with the patient by means of a third line of the fluid lines, in particular, directly.

A fourth line of the fluid lines can be fluid-connected with the oxygenator at one end. In addition, the fourth line can be fluid-connected with a gas source at another end. The gas source can be a stationary gas supply, a gas cylinder or a pneumatic control unit. As already described above the blood pump can be driven currentless. For this the blood pump can be fluid-connected with a fifth line of the fluid lines, in particular, several fifth lines. The fifth line can be fluid-connected with the gas source at another end.

The fourth line and the fifth line can be fluid-connectable with the same gas source. In addition, the fourth line and the fifth line can be connectable with the same device for controlling or regulating a gas volume flow in the fourth line and/or the fifth line or the fifth lines. The device can, in particular, be fluid-connectable with the fourth line and/or the fifth line.

The handle of the carrying case can be arranged outside of the carrying case housing. The carrying case can therefore be carried in a simple way by means of the handle. As a result, the holding means fulfils several functions, such as for example to allow a carrying of the carrying case, permanently aligning the oxygenator and the blood pump with each other, protecting fluid lines entering and leaving the carrying case and giving these a direction, and preventing a relative movement between the oxygenator and the blood pump.

The carrying case can have a fitting means for fitting the carrying case to an object, such as for example a hospital bed. The fitting means can be connected with the carrying case, in particular the carrying case housing, on one side and/or to the object with the frame of the holding means lying in the same on the other side in a fixed or moveable way.

The fitting device can have a holder and a holder mounting. The holder can be arranged in one position in the holding mounting. The carrying case is not connected with the hospital bed in this position. In addition, the holder can partly protrude from the holder mounting in another position. In this position the carrying case can be connected with the hospital bed. The holder can be of a heel-shaped design at its respective ends. The two heel-shaped ends can be connected with each other by an intermediate bridge, wherein the intermediate bridge has a U-shaped section. The intermediate bridge is turned by 90° when the holder is transferred from this position into another position. The holder can be turned no further from the other position. A further turning of the holder is prevented in that the U-shaped section bumps against a plate of the fitting device and a further turning of the heel-shaped ends is thus prevented in a simple way.

The holder can be moveably connected with the carrying case housing and/or the frame, and in particular guided out of the holder mounting through folding, pivoting or plugging. As a result, the carrying case can be connected with the hospital bed in a simple way.

The carrying case can be of a sterile design. With this design the holding means, the oxygenator and the blood pump cannot be replaced by the user of the carrying case.

Alternatively, the carrying case can have a set of interchangeable oxygenators and/or a set of interchangeable blood pumps and/or a set of interchangeable holding means. In this case the user can pre-configure the carrying case. The user can, in particular, select a single oxygenator from the set of oxygenators, a single blood pump from the set of blood pumps, and a single holding means from the set of holding means. The selected oxygenator and the selected blood pump are connected with the selected holding means. This design offers the advantage that use of the carrying case is flexible.

The carrying case can have a determining means, in particular, a spirit level, for determining an alignment of the carrying case. The determining means can be arranged in a gap of the carrying case housing. The determining means can, in particular, be arranged in a gap provided in the first housing section and/or second housing section. The alignment of the carrying case in at least one direction, in particular in two directions, can be determined by means of the determining means. The alignment of the carrying case in a horizontal direction can be calculated by means of the determining means here. Providing the determining means makes it possible in a simple way to ensure that the carrying case is deposited on a horizontal level during use. This is important in order to ensure that the oxygenator inlet is arranged in a vertical direction above the blood pump outlet during use.

A heart-lung machine with a carrying case according to the invention, the gas source and the device for controlling or regulating, which controls or regulates a volume flow of the gas supplied to the oxygenator and the blood pump is of particular advantage. The device can be fluidically arranged between the gas source and the carrying case and/or is in fluid-connection with the gas source and the carrying case.

BRIEF DESCRIPTION OF THE DRAWINGS

The object of the invention is schematically illustrated in the Figures and is described below with reference to the Figures, wherein identical elements or those that act identically are usually identified with the same reference numbers. Shown are.

DETAILED DESCRIPTION

Figure 1:
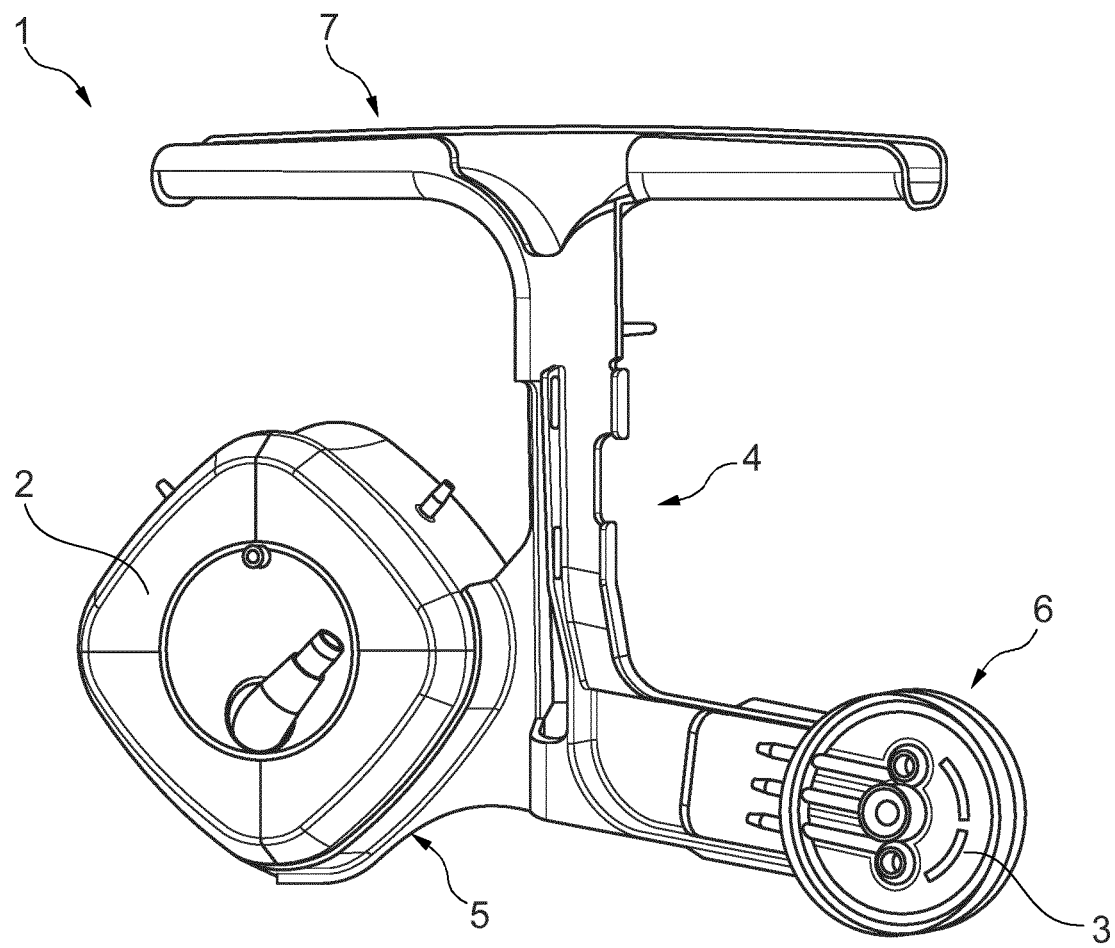
FIG. 1 an illustration of a holding means according to the invention.
Figure 3:
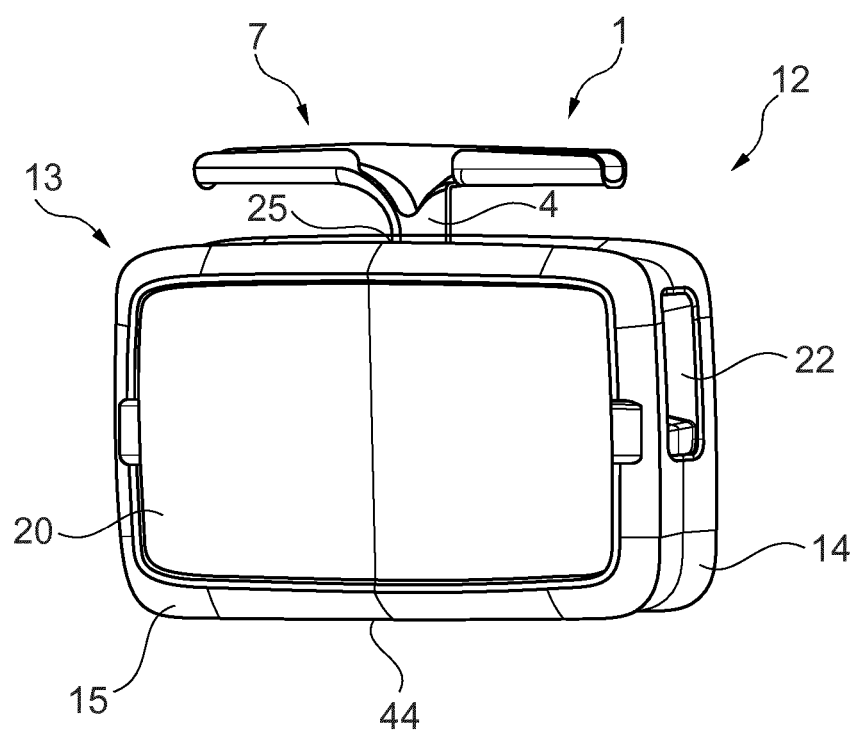

A holding means 1 shown in FIG. 1 for holding an oxygenator 2 and a blood pump 3 has a frame 4. The frame 4 can be connected with a carrying case housing 13 in a torque-proof way as shown in FIG. 3 and serves for fitting the oxygenator 2 and the blood pump 3 relative to each other. The frame 4 has a frame section 5 and another frame section 6. The oxygenator 2 is connected with the frame section 5 in a torque-proof way and the blood pump 3 is connected with the other frame section 6 in a torque-proof way.

The holding means 1 also has a handle 7, which is connected with the frame 4 in a torque-proof way. The handle 7 is, in particular, designed as a single piece with the frame 4. The handle 7 is connected with one end of the frame 4 in a torque-proof way here. The frame section 5 and the other frame section 6 are arranged at another end of the frame 4.

Figure 7:
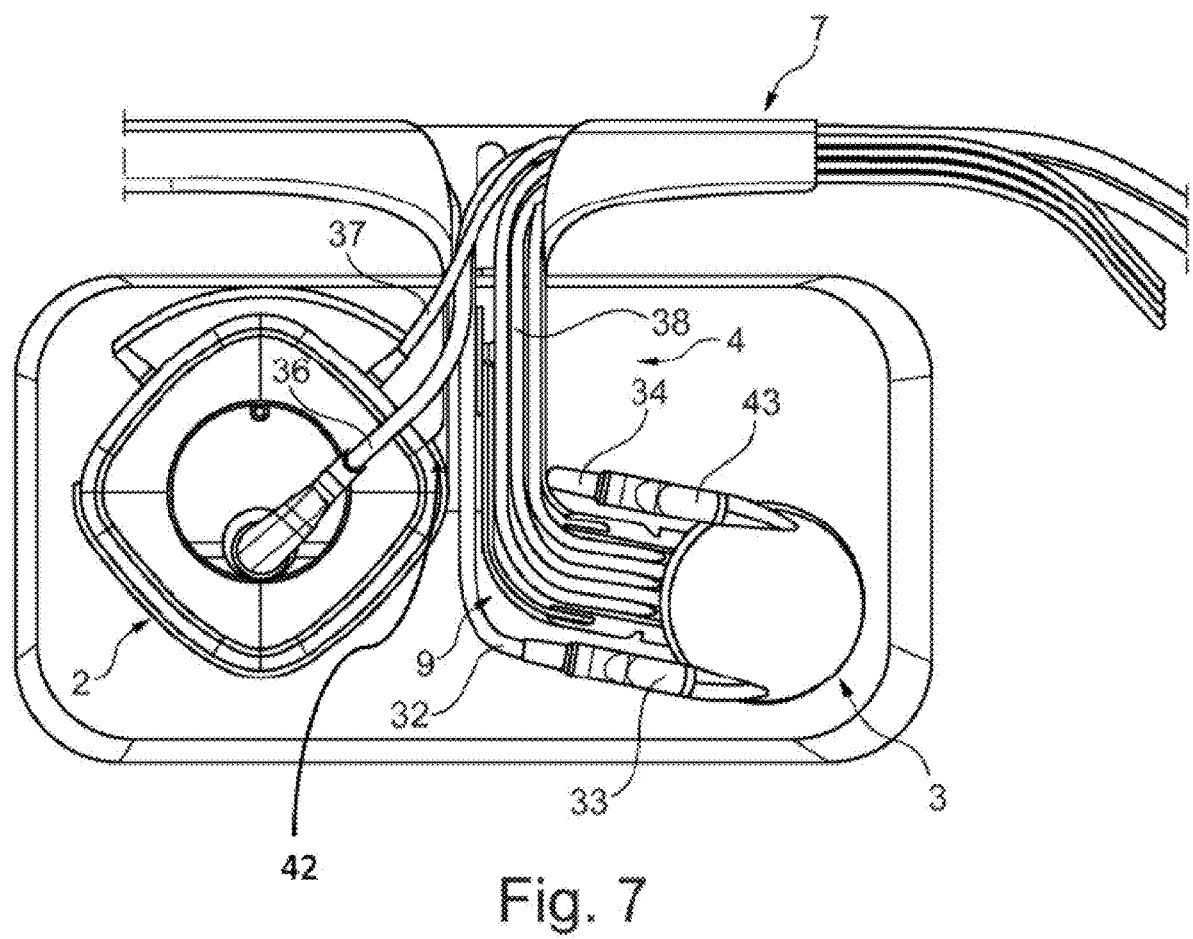

The frame section 5 and the other frame section 6 are arranged in such a way that an oxygenator is arranged closer to the handle 7 than a blood pump outlet 43 shown in FIG. 7, wherein the blood flowing from the blood pump outlet 43 flows into the oxygenator 2 via the oxygenator inlet. The blood pump outlet 43 is therefore arranged further away than the oxygenator inlet 42, viewed from the handle 7 in a vertical direction, so that the direction of the blood flowing out of the blood pump 3 points diagonally upwards. The blood pump 3 is, in particular, arranged in such a way that blood exiting from the blood pump 3 flows in a direction towards the handle 7. The blood flow direction rises in a vertical direction between the blood pump 3 and the oxygenator 2.

Figure 2:
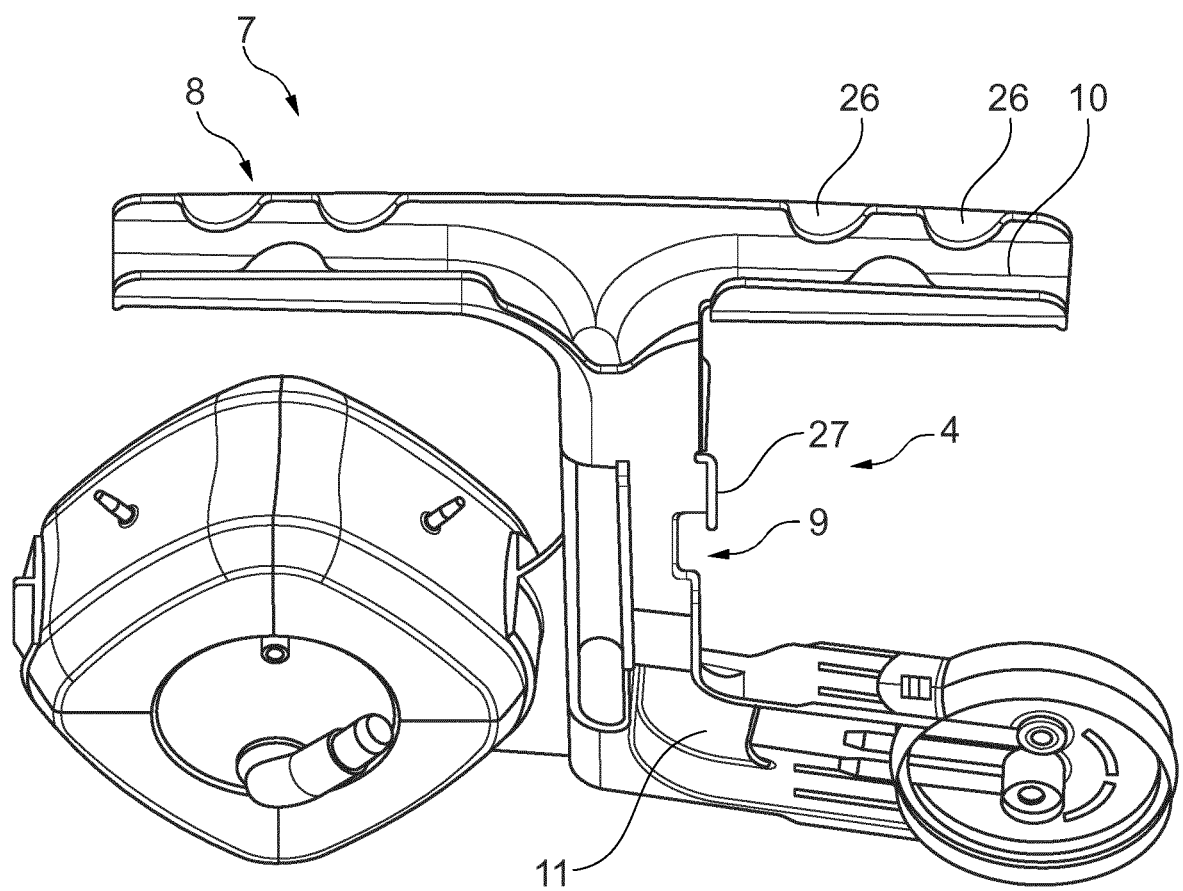
FIG. 2 an illustration of the holding means according to the invention diagonally from above, FIG. 3 an illustration of a carrying case according to the invention according to a first embodiment example, FIG. 4 an illustration of a first housing section of the carrying case according to the invention according to the first embodiment example, FIG. 5 an illustration of a second housing section of the carrying case according to the invention according to the first embodiment example, FIG. 6 an illustration of the carrying case according to the invention according to the first embodiment example without a closing cover, FIG. 7 a side section illustration of a carrying case according to the invention according to a second embodiment example with several fluid lines, FIG. 8 use of the carrying case according to the invention according to the second embodiment example in a hospital room, FIG. 9 use of the carrying case according to the invention according to the second embodiment example in an emergency situation, FIG. 10 an illustration of part of the carrying case according to the invention according to a third embodiment example, wherein a holder of a fitting device is in a folded position, FIG. 11 an illustration of the carrying case according to the invention according to the third embodiment example, wherein the holder is in an unfolded position.

FIG. 2 shows the holding means 1 from a different viewing angle than that of FIG. 1. As is clear from FIG. 2 the handle 7 has a guide 8. The guide 8 serves for guiding fluid lines illustrated in FIG. 7 and has a gap 10, in which the fluid lines shown in FIG. 7 are arranged. In addition, the guide 8 has several protrusions 26, which protrude radially inwards and prevent the fluid lines from falling out of the guide 8.

The frame 4 of the holding means 1 has another guide 9 for guiding at least one fluid line. The other guide 9 has another gap 11, in which the at least one fluid line is arranged. The other guide 9 has side walls 27, which prevent the fluid line from falling out of the other guide 9.

FIG. 3 shows a carrying case 12 according to the invention with the holding means 1, which is connected with a carrying case housing 13 in a torque-proof way and is partly arranged in the carrying case housing 13. As is clear from FIG. 3 the handle 7 is arranged outside of the carrying case housing 13. In addition, a part of the frame 4 protrudes from the carrying case housing 13 through a passage opening 25.

The carrying case housing 13 has a first housing section 14 and a second housing section 15, which are connected with each other in a torque-proof way. The carrying case 12 also has a closing cover 20, which covers part of the second housing section 15.

A further passage opening 22 is provided on one side of the carrying case 12. A branch line, not illustrated, can extend through the further passage opening 22 and is in fluid-connection with one end of an analysis means not illustrated here. The blood extracted from the patient can be analysed in the analysis means. The other end of the branch line not illustrated here is connected with a connector, via which blood can be branched off.

The carrying case 12 has a footprint 44, with which the carrying case 12 is placed on a positioning surface, such as for example a floor. The footprint 44 is arranged at an end of the carrying case 12 that lies opposite the handle 7 relative to a horizontal level. When the carrying case 12 is placed on the floor with its footprint 44 the carrying case 12 is aligned in such a way that the oxygenator inlet is arranged in a vertical direction above the blood pump outlet.

Figure 4:
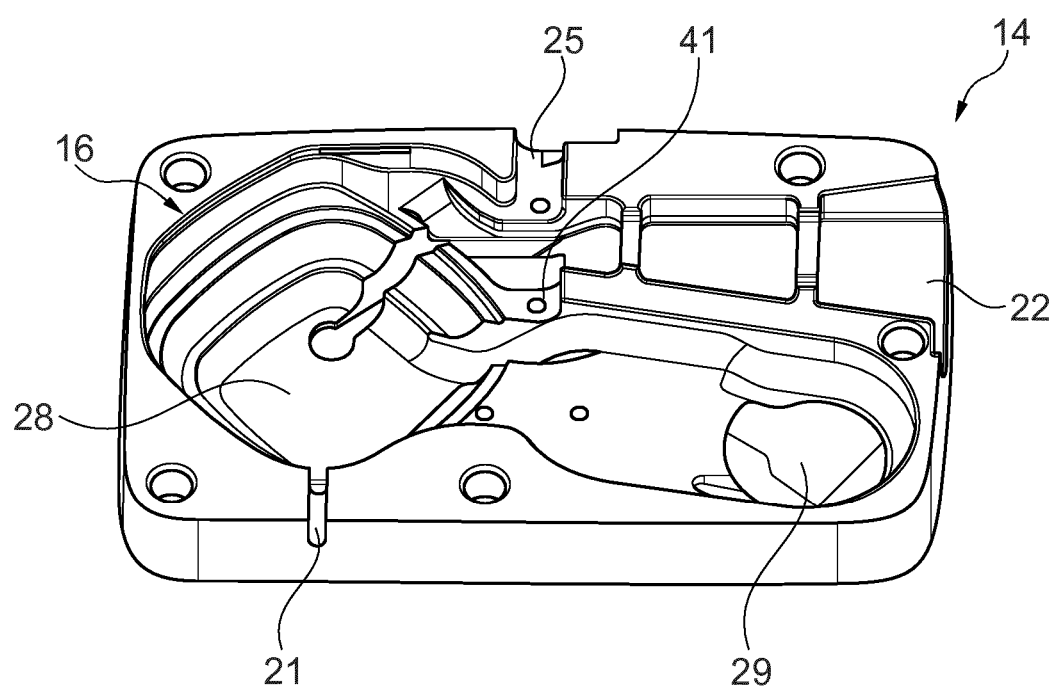

FIG. 4 shows a perspective illustration of the first housing section 14. The first housing section 14 has a first mounting 16. The first mounting 16 serves for receiving a part of the frame 4, the oxygenator 2 and the blood pump 3. The first mounting 16 has a part 28 that serves for receiving the oxygenator 2 for this. In addition, the first mounting 16 has another part 29 that serves for receiving the blood pump 3. In addition, the first mounting 16 has a further part 41 that serves for receiving a part of the frame 4.

The first housing section 14 delimits the passage opening 25 and the further passage opening 22 together with the second housing section 15. In addition, the first housing section 14 delimits a fluid outlet passage 21 together with the second housing section 15. The fluid outlet passage 21 formed jointly with the second housing section makes it possible that a fluid, such as for example condensate water, can flow out of the carrying case 12.

Figure 5:
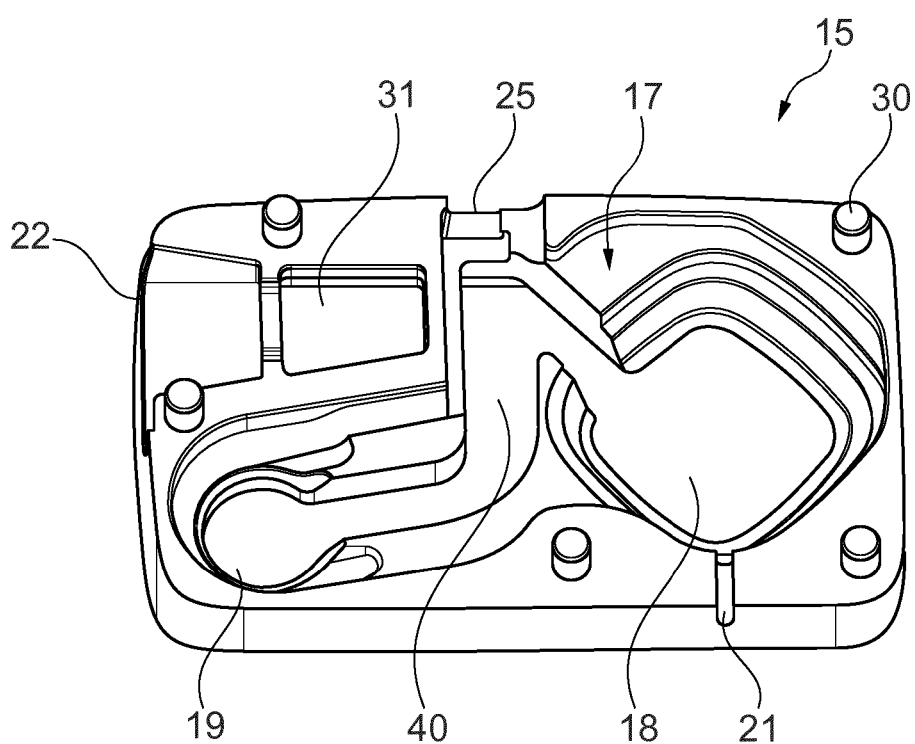

FIG. 5 shows a perspective illustration of the second housing section 15. The second housing section 15 has a second mounting 17. The second mounting 17 serves for receiving a part of the frame 4, the oxygenator 2 and the blood pump 3. The second mounting 17 has a part 18 that serves for receiving the oxygenator 2, and another part 19 that serves for receiving the blood pump 3 for this. Part 18 as well as the other part 19 of the second mounting 17 are designed as an opening. In addition, the further part 40 of the second mounting 17 receiving the part of the frame 4 is designed as an opening.

The second housing section 15 has several elevations 30, which enter corresponding holes provided in the first housing sections 14 for a connection with the first housing section 14. In addition, the second housing section 15 has a recess 31, which is also designed as an opening.

Figure 6:
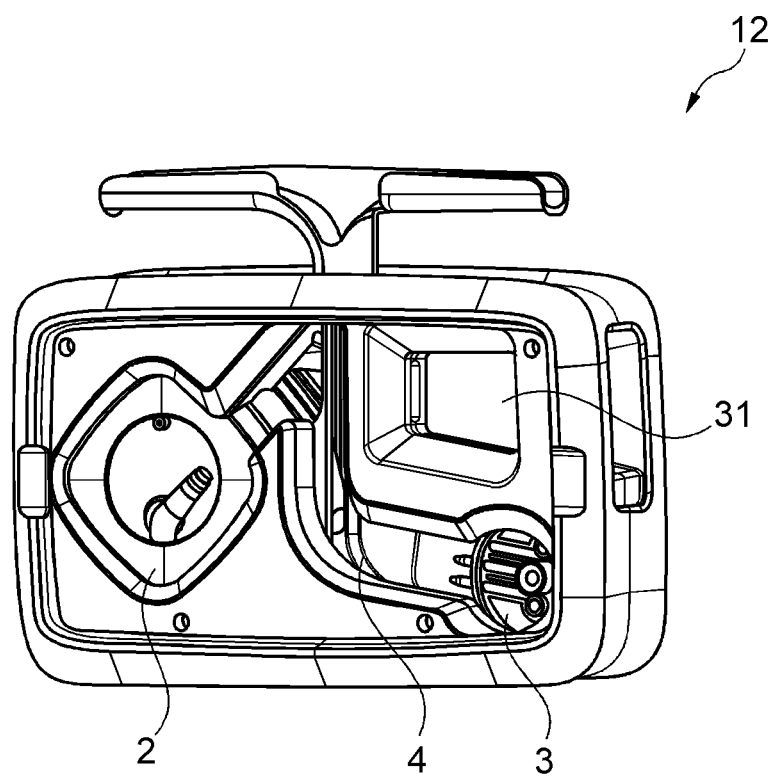

FIG. 6 shows a carrying case 12 without the closing cover 20. As is clear from FIG. 6 a part of the oxygenator 2, a part of the blood pump 3 and a part of the frame 4 are released due to the design of the second gap 17 described above. This means that the components are visible from the outside. Spare parts and/or sensors and/or the branch line can be arranged in the gap 31.

The first mounting 16 of the first housing section 14 and the second mounting 17 of the second housing section 15 form a hollow space, in which the oxygenator 2, a part of the frame 4 and the blood pump 3 are arranged in such a way that they cannot move relative to each other and/or not relative to the carrying case housing 13.

FIG. 7 shows a side section illustration of the carrying case 12 according to a second design with several fluid lines. The section is realised in such a way that the inside of the carrying case housing 13 is visible. As is clear from FIG. 7 the oxygenator 2 and the blood pump 3 are each fluid-connected with several fluid lines.

The fluid lines include a first line 32, which is fluid-connected with a blood pump inlet 33 at one end. The first line 32 is fluid-connected with the patient at another end. A second line 34 of the fluid lines is fluid-connected with a blood pump outlet 43 at one end. In addition, the second line 34 is fluid-connected with the oxygenator 2, in particular, with the oxygenator inlet, at another end. The blood flowing into the oxygenator 2 flows back to the patient via a third line 36 following the gas exchange.

In addition, the oxygenator 2 is fluid-connected with a fourth line 37. The oxygenator 2 is supplied with has via the fourth line 37. One end of the fourth line 37 is fluid-connected with a gas source not illustrated in FIG. 3, such as for example a gas tank or a pneumatic control console.

The blood pump 3 is fluid-connected with three fifth lines 38. The blood pump 3 is supplied with gas, such as for example oxygen or air, by means of the fifth lines 38, or the same is vented from the same. The supply or venting of gas can realise a pump effect, which lastly effects a blood volume flow through the oxygenator 2.

With the carrying case 12 illustrated in FIG. 7 all fluid lines are guided through the handle 7. All fluid lines extend in the same direction. The three fifth lines 38 are guided through the other guide 9 of the frame 4.

Figure 8:
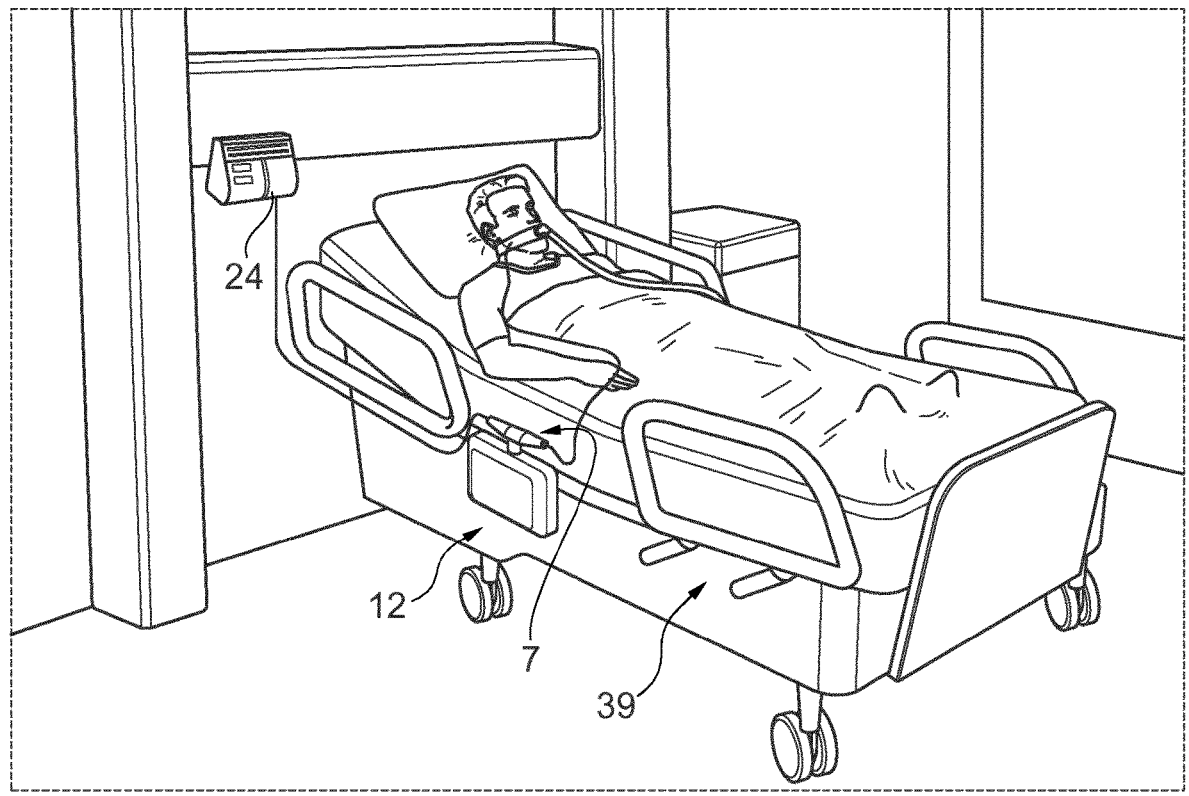

FIG. 8 shows the use of the carrying case 12 illustrated in FIG. 3 in a hospital room. The carrying case 12 is attached to a hospital bed 39. A patient from whom blood is extracted, which then flows to the carrying case 12, lies in the hospital bed 39. The blood enriched with oxygen in the oxygenator then flows back to the patient.

The carrying case 12 is also fluid-connected with a device 24 for controlling or regulating a gas volume flow in the fluid lines by means of the fluid lines. The blood volume flow conveyed by the blood pump 3 and the gas volume flow supplied to the oxygenator 2 can be controlled or regulated by controlling or regulating the gas volume flow in the fluid lines. The device 24 is attached to a wall of the hospital room with this application and is fluid-connected with the oxygenator 2 and/or the blood pump 3 via fluid lines. The device 24 is fluid-connected with at least one gas source not illustrated here.

The design illustrated in FIG. 8 differs from the design illustrated in FIG. 7 in that the fluid lines in fluid connection with the patient extend from the handle 7 in another direction than the other fluid lines connected with the device 24. The fluid lines in fluid connection with the patient can also extend in different directions if patient access is realised at different body points.

Figure 9:
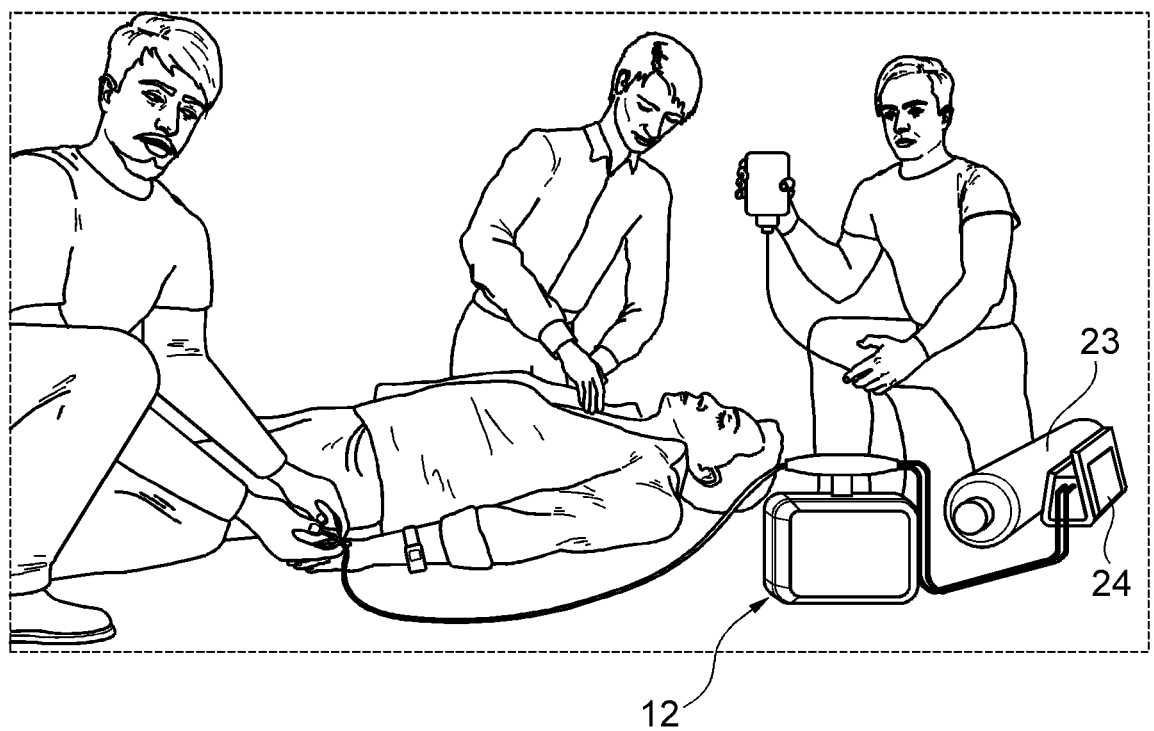

FIG. 9 shows the use of the carrying case 12 illustrated in FIG. 3 in an emergency situation, where a patient lying on the floor is suffering from acute heart or lung insufficiency. The carrying case 12 is placed on the floor. It is clear from FIG. 9, as with FIG. 8, that the carrying case 12 is fluid-connected with the patient via respective fluid lines. In addition, it is clear from FIG. 9 that the carrying case 12 is fluid-connected with the device for controlling or regulating 24. The device for controlling or regulating 24 is fluid-connected with the gas source 23, wherein the device 24 is fluidically arranged between the gas source 23 and the carrying case 12.

Figure 10:
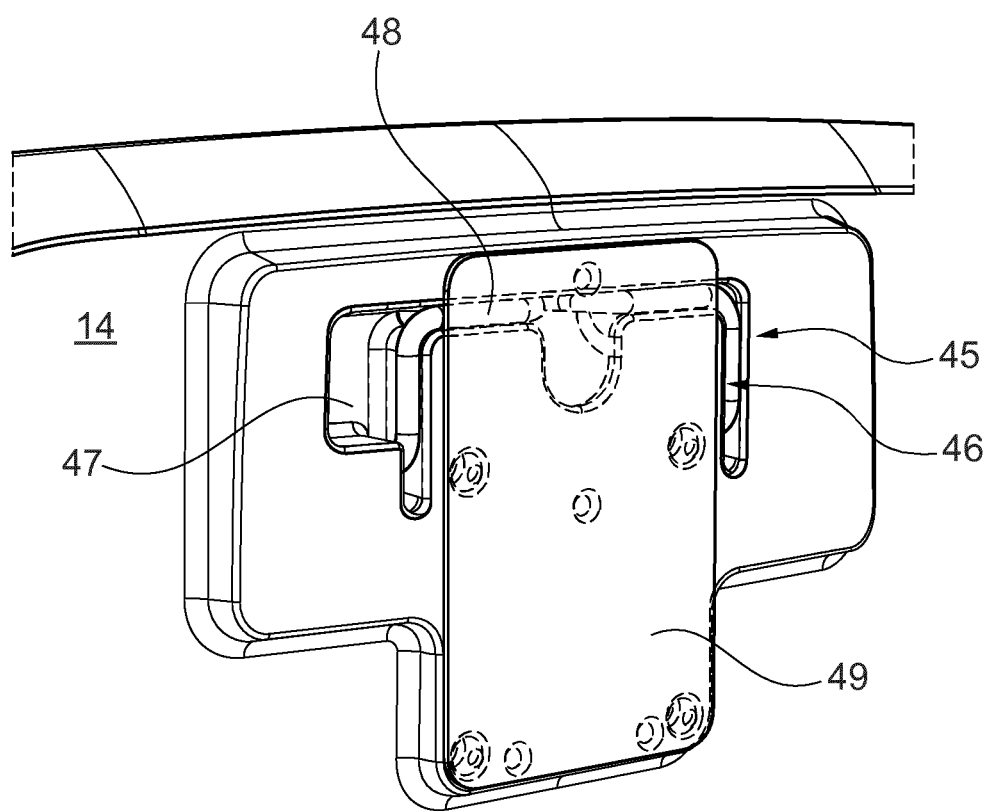

FIG. 10 shows an illustration of a part of the carrying case 12 according to the invention according to a third embodiment example. The carrying case 12 has a fitting device 45, which is fitted on the first housing section 14. The fitting device 45 has a holder 46 and a holder mounting 47. As is clear from FIG. 11 the holder 46 is of a heel-shaped design at both its ends. The two heel-shaped ends are connected with each other by an intermediate bridge 48. The intermediate bridge 48 has a central U-shaped section. The intermediate bridge 48 is visible in FIG. 10, as a plate 49 of the fitting device 45 is illustrated partly transparent. The plate 49 covers a part of the holding mounting 47.

With the position of the holder 46 illustrated in FIG. 10 this is arranged in the holder mounting 47. The carrying case 12 cannot be connected with the hospital bed in this position of the mounting 46.

Figure 11:
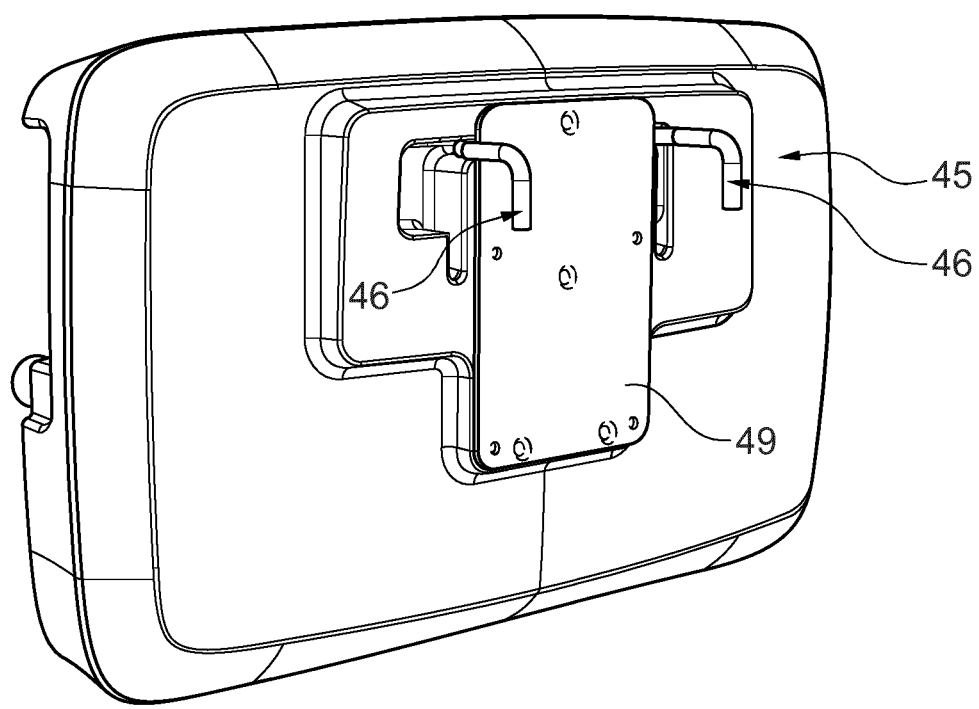

FIG. 11 shows the carrying case 12 according to the third design, wherein the holder 46 is in an unfolded position. The heel-shaped ends of the holder 46 each protrude from the holder mounting 47 and the first housing section 14 and can be connected with the hospital bed that is not illustrated.

The holder 46 is turned in one direction for transferring the holder 46 from the folded position illustrated in FIG. 10 into the unfolded position shown in FIG. 11. A further turning of the holder in this direction is not possible, as the U-shaped section of the intermediate bridge 48 bumps against the plate 49 and thus prevents a further turning of the holder 46. The U-shaped section is arranged in the gap visible in FIG. 10 in the position of the holder 46 illustrated in FIG. 11.

LIST OF REFERENCE NUMBERS

1 Holding means
2 Oxygenator
3 Blood pump
4 Frame
5 Frame section
6 Other frame section
7 Handle
8 Guide
9 Other guide
10 Gap
11 Other gap
12 Carrying case
13 Carrying case housing
14 First carrying case section
15 Second carrying case section
16 First mounting
17 Second mounting
18 Part of second mounting
19 Other part of second mounting
20 Closing cover
21 Fluid outlet passage
22 Further passage opening
23 Gas source
24 Device for controlling or regulating
25 Passage opening
26 Protrusion
27 Side wall
28 Part of first mounting
29 Other part of first mounting
30 Elevation
31 Recess
32 First line
33 Blood pump inlet
34 Second line
36 Third line
37 Fourth line
38 Fifth line
39 Hospital bed
40 Further part of second mounting
41 Further part of first mounting
43 Blood pump outlet
44 Footprint
45 Fitting means
46 Holder
47 Holder mounting
48 Intermediate bridge
49 Plate

The invention claimed is:
1. A system comprising:
a frame configured to hold an oxygenator and a blood pump, wherein the frame comprises,
 a first frame section configured to be coupled to the oxygenator in a torque proof way, and
 a second frame section configured to be coupled to the blood pump in a torque proof way,
 and a handle, connected to the first and second frame sections, and
a carrying case, comprising,
 a carrying case housing, wherein the carrying case housing is configured to receive the frame,
wherein the carrying case housing is configured to hold the frame, and
wherein the frame is configured to be partly arranged in the carrying case housing with the handle arranged outside of the carrying case housing.
2. A system according to claim 1, wherein the handle is connected with the frame in a torque-proof way.
3. A system according to claim 2, wherein,
 a. the handle has a guide for guiding a fluid line or several fluid lines, or
 b. the handle has a guide, designed in such a way that several fluid lines can be guided in the same direction or in different directions.
4. A system according to claim 3, wherein,
 a. the guide has a gap, in which the fluid line or fluid lines can be arranged.
5. A system according to claim 1, wherein,
 a. the oxygenator and the blood pump can be arranged by the first frame section and the second frame section in such a way that the distance between an oxygenator inlet and the handle is shorter than the distance between a blood pump outlet and the handle.
6. A system according to claim 1, wherein,
the frame is connected with a carrying case housing in a torque-proof way.
7. A system according to claim 6, wherein the carrying case housing has a first housing section and a second housing section, wherein
 a. the first housing section and the second housing section are disconnectably connected with each other in a torque-proof way, or wherein
 b. at least one of the first housing section and the second housing section comprise a non-transparent material, or wherein
 c. the first housing section comprises at least one foam material or the second housing section comprises at least one foam material.
8. A system according to claim 1, wherein the carrying case housing has a first housing section and a second housing section, and
 a first mounting of the first housing section and a second mounting of the second housing section forming a hollow space, in which a part of the frame or the oxygenator or the blood pump is arranged, and wherein at least a part of the frame or the oxygenator or the blood pump are at least partly embedded in the first housing section and the second housing section.
9. A system according to claim 8, wherein the second housing section comprise a recess, and
 wherein the second mounting comprises,
 a. a part of the second mounting receiving the oxygenator is designed as an opening for partly releasing the oxygenator, or
 b. another part of the second mounting receiving the blood pump is designed as an opening for partly releasing the blood pump, or c. a further part of the second mounting receiving the frame is designed as an opening for partly releasing the frame.

10. A system according to claim 9 wherein the carrying case has a closing cover for closing one or more openings of the second mounting.

11. A system according to claim 1, wherein the carrying case housing has a first housing section and a second housing section, and wherein one or both of the first housing section and the second housing section have a passage opening,
   a. through which a fluid line that is fluid-connected with one or both of the oxygenator and the blood pump leaves the carrying case housing or through which several fluid lines that are fluid-connected with one or both of the oxygenator and the blood pump leave the carrying case housing or
   b. through which a part of the frame extends.

12. A system according to claim 1,
   a. wherein the carrying case housing has a first housing section and a second housing section, the carrying case has a fluid outlet passage, through which a fluid can flow out of one or both of the first housing section or the second housing section or
   b. wherein the carrying case has a further passage opening, through which at least one branch line extends for supplying blood to an analysis means.

13. A system according to claim 1, wherein
   a. the blood pump can be driven currentless or
   b. the blood pump can be driven by means of a gas flowing in one or in several fluid lines.

14. A system according to claim 1, wherein a footprint, is configured in such a way that an oxygenator inlet is arranged in a vertical direction above a blood pump outlet when the carrying case is placed on a positioning surface with the footprint.

15. A system according to claim 1, wherein
   a. at least one fluid line, at least one branch line, or both are configured such that at least part of the fluid line or at least part of the branch line extending from the carrying case housing is retractable into the carrying case housing or
   b. the carrying case is connected with at least one fluid line, at least one branch line, or both in such a way that a retraction of at least part of the fluid line or at least part of the branch line protruding from the carrying case housing can be prevented.

16. A system according to claim 1, wherein the carrying case is of a sterile design.

17. A system according to claim 1, wherein the carrying case has at least one of a set of interchangeable oxygenators, a set of interchangeable blood pumps, or a set of interchangeable holding means.

18. A heart-lung machine with a system according to claim 1, comprising a gas source and a device for controlling or regulating a blood volume flow flowing through the blood pump and a gas volume flow flowing through the oxygenator, connected with the gas source and the carrying case.

19. A system according to claim 2, wherein the frame has a guide for guiding a fluid line or several fluid lines.

20. A system according to claim 19, wherein, the guide has a gap, in which the fluid line can be arranged.

* * * * *